United States Patent [19]

Kane

[11] 4,089,876

[45] May 16, 1978

[54] METHOD FOR REACTING 2-AROMATIC SUBSTITUTED 1,3-DITHIANES WITH α,β-UNSATURATED KETONES TO SELECTIVELY PRODUCE 1,4- OR 1,2-ADDITION PRODUCTS AND THE PRODUCTS MADE THEREBY

[75] Inventor: Vinayak V. Kane, Princeton, N.J.

[73] Assignee: Ortho Pharmaceutical Corporation, Raritan, N.J.

[21] Appl. No.: 707,965

[22] Filed: Jul. 23, 1976

[51] Int. Cl.$^2$ .............................................. C07D 339/08
[52] U.S. Cl. ............................ 260/327 M; 260/330.5; 260/332.3 R; 260/332.3 H; 260/332.3 P; 424/277
[58] Field of Search .......... 260/327 M, 609 R, 609 F, 260/330.5, 332.3 R, 332.3 H, 332.3 P

[56] References Cited

PUBLICATIONS

Seebach, et al., J. Org. Chem., vol. 40, No. 2, 1975, pp. 231-237.
Bonnet, et al., C.A. 77:61307s (1972).
Trost, et al., J.A.C.S. 97:24, Nov. 26, 1975, pp. 7152-7157.

*Primary Examiner*—Cecilia M. Jaisle
*Attorney, Agent, or Firm*—Benjamin F. Lambert

[57] ABSTRACT

Method for reacting a 2-aromatic substituted 1,3-dithiane with an α,β-unsaturated ketone to selectively produce either the 1,4-addition product or the 1,2-addition product and the products made thereby. The 1,2- and 1,4-addition products possess cardiovascular activity, particularly antihypertensive and antiarrythmic activity.

14 Claims, No Drawings

METHOD FOR REACTING 2-AROMATIC SUBSTITUTED 1,3-DITHIANES WITH α,β-UNSATURATED KETONES TO SELECTIVELY PRODUCE 1,4- OR 1,2-ADDITION PRODUCTS AND THE PRODUCTS MADE THEREBY

DESCRIPTION OF THE INVENTION

This invention relates to a method for reacting a 2-aromatic substituted, 1,3-dithiane with an α,β-unsaturated ketone to selectively produce either the 1,4-addition product or the 1,2-addition product and to the products made thereby.

The subject method may be illustrated by the following:

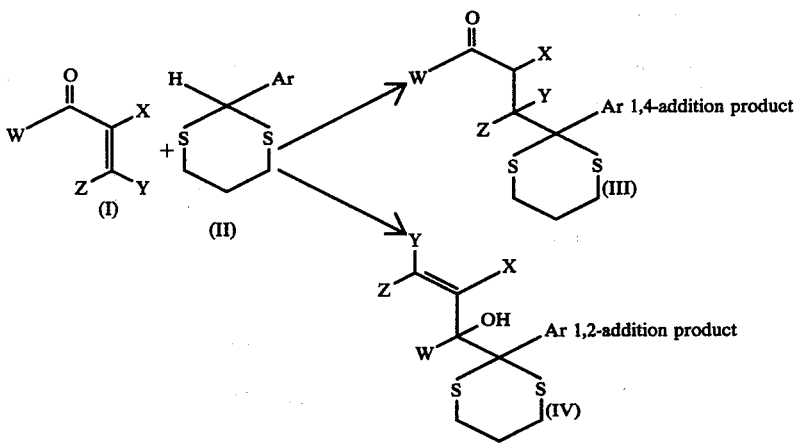

wherein the identities of W, X, Y, and Z have no effect on the course of the reaction; and Ar is an aromatic group. The subject method permits the selective production of either the 1,2- or the 1,4-addition product for any 2-aromatic substituted 1,3-dithiane and α,β-unsaturated ketone which will react. It is recognized that certain 2-aromatic substituted 1,3-dithianes and α,β-unsaturated ketones may not react at all (e.g., because large substituent groups cause steric hinderance to the reaction). However, it is a matter of routine experimentation to determine whether the subject method will function for particular reactants.

The subject compounds may be illustrated by formulas III and IV above.

More specifically, the method of the invention comprises deprotonating an aromatic dithiane of formula II, e.g., with a suitable base such as butyllithium (which is preferred), an alkali metal hydride such as sodium hydride or potassium hydride, lithium diisopropylamide, or the like, in a suitable anhydrous aprotic solvent such as tetrahydrofuran (THF), 1,2-dimethoxyethane or the like at reduced temperature (preferably, from about −75° C. to about −100° C.) to generate the corresponding 2-carbanion

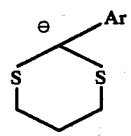

This 2-carbanion is then mixed at reduced temperature with an α,β-unsaturated ketone of formula I. If a 1,2-addition product is desired, the reaction mixture is maintained at the reduced temperature and allowed to react, after which a protonating solvent is added to protonate any unreacted base and carbanion and thus "quench" the reaction at this reduced temperature. The reaction mixture is then allowed to warm to ambient temperature. If a 1,4-addition product is desired, the reaction mixture is first allowed to warm to ambient temperature (e.g., above about 10° C.), and is allowed to react, after which a protonating solvent is added (at ambient temperature) to quench the reaction. Water is the preferred protonating solvent, but other known protonating solvents may be used (e.g., lower alkanols). Either product may be isolated from its respective reaction mixture by techniques commonly used in the chemical art; e.g., extraction with an organic solvent such as an ether (e.g., diethyl ether), a halocarbon (e.g., chloroform), ethyl acetate, or the like, followed by chromatographing the residue obtained by removing the extracting solvent.

The 1,4-addition product is the thermodynamically-preferred product, and hence is the one formed when the reaction mixture is allowed to warm to ambient temperature prior to quenching. The 1,2-addition product, on the other hand, is the kinetically-preferred product, and hence is the one formed if the reaction mixture is quenched prior to being allowed to warm to ambient temperature.

Preferred subject compounds produced by 1,4-addition may be illustrated by the following:

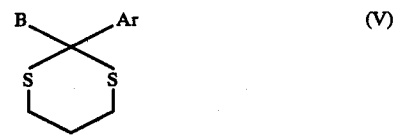

wherein Ar is an aromatic group and B is a member selected from the group consisting of:

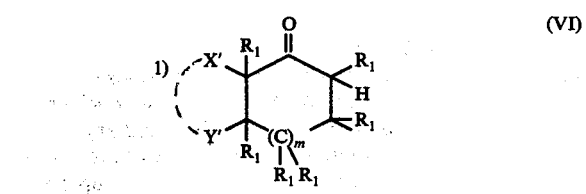

wherein, each $R_1$ is a member selected from the group consisting of hydrogen and lower alkyl;

X' and Y' taken separately are each members selected from the group consisting of hydrogen and lower alkyl; X' and Y' taken together is —[CH$_2$]$_n$— where $n$ is an integer from 2 to 6; and $m$ is an integer from 0 to 7;

2) 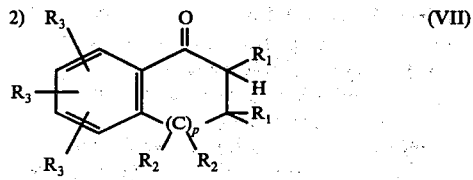 (VII)

wherein; each R$_1$ is a member selected from the group consisting of hydrogen and lower alkyl;
each R$_2$ is lower alkyl; $p$ is an integer from 0 to 3; and
each R$_3$ is a member selected from the group consisting of hydrogen, lower alkyl, lower alkoxy, phenoxy, substituted phenoxy, nitro, diloweralkylamino, and methylenedioxy, provided that not more than one R$_3$ is a methylenedioxy;

3) 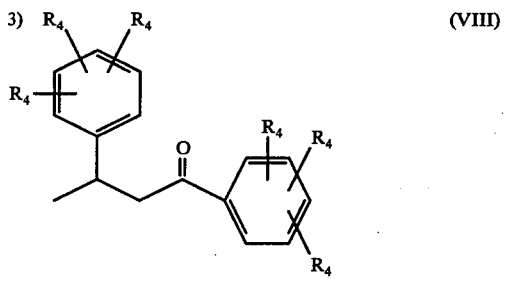 (VIII)

wherein, each R$_4$ is a member selected from the group consisting of hydrogen, lower alkyl, lower alkoxy, nitro, phenoxy, substituted phenoxy, diloweralkylamino, and methylenedioxy, provided that not more than one R$_4$ on each phenyl ring is methylenedioxy;

4) 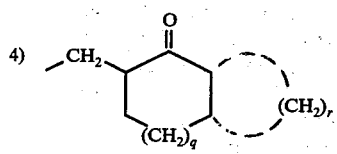 (IX)

wherein,
$q$ is an integer from 0 to 2; and
$r$ is an integer from 3 to 6; and

5) 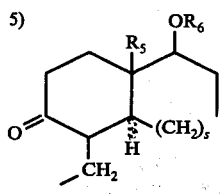 (X)

wherein,
$s$ is an integer from 0 to 2;
R$_5$ is a member selected from the group consisting of hydrogen and lower alkyl, and R$_6$ is a member selected from the group consisting of lower alkyl and aryl.

More preferred compounds of formula (V) are those wherein Ar is a member selected from the group consisting of phenyl; phenyl substituted with from one to three members selected from the group consisting of lower alkyl, lower alkoxy, phenoxy, substituted phenoxy, nitro, dilower alkylamino, and methylenedioxy, provided that not more than one of said members is methylenedioxy ("substituted phenyl"); naphthyl; naphthyl substituted with from one to three members each selected from the group consisting of lower alkyl, lower alkoxy, phenoxy, substituted phenoxy, nitro, diloweralkylamino, and methylenedioxy; 2-thienyl; 2-thienyl substituted with from one to three lower alkyls;

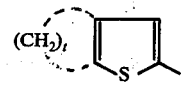

wherein $t$ is an integer from 3 to 5; and

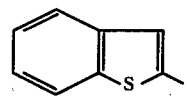

Also included within the scope of the invention are the corresponding preferred 1,2-addition products of formula V wherein B is a member selected from the group consisting of:

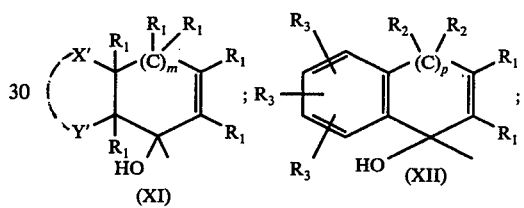

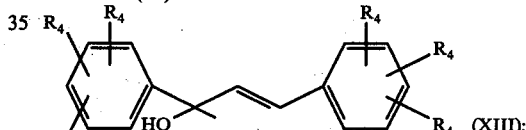

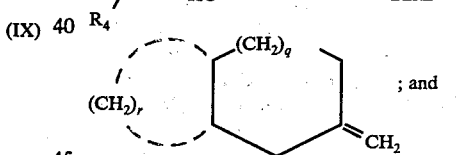

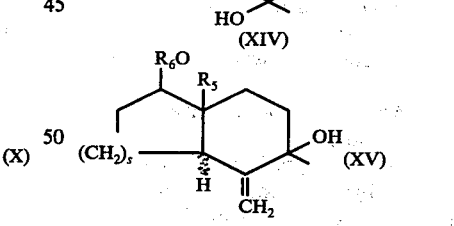

wherein R$_1$, R$_2$, R$_3$, R$_4$, R$_5$, R$_6$, $m$, $n$, $p$, $q$, $r$, $s$, X', and Y' are as previously defined and Ar is an aromatic group. More preferred 1,2-addition products are those wherein Ar is as defined in the immediately preceding paragraph.

As used herein, the terms "lower alkyl" and "lower alkoxy" mean straight or branched chain saturated, aliphatic hydrocarbon radicals having up to six carbon atoms, such as for example, methyl, ethyl, isopropyl, 2-pentyl, hexyl, and the like lower alkyls, and correspondingly, methoxy, ethoxy, isopropoxy, 2-pentoxy, hexoxy, and the like lower alkoxys. The term "aromatic group" as used herein refers to any aryl or heterocyclic aromatic group which functions to stabilize the carbanion produced from the dithiane of formula II upon reaction with a deprotonating agent such as a suitable base; e.g., butyllithium. "Aryl" includes phenyl; "substituted phenyl" defined as phenyl substituted with from one to three members selected from the group consisting of lower alkyl, lower alkoxy, phenoxy, substituted phenoxy, halo, nitro, diloweralkylamino, and methylenedioxy (provided that not more than one of said members is methylenedioxy); polynuclear aromatic radicals such as naphthyl, phenanthryl, anthracyl, and the like; and polynuclear aromatic radicals substituted with from one to three members each selected from the group consisting of lower alkyl, lower alkoxy, phenoxy, substituted phenoxy, nitro, diloweralkylamino, and methylenedioxy. Fused ring aryl compounds having three or less aromatic rings are preferred. The term "heterocyclic aromatic" includes radicals derived from five- and six-membered rings containing one or more of the heteroatoms O, S, and N as well as radicals derived from fused ring systems containing one or more of the heteroatoms O, S, and N. Examples of compounds from which these radicals may be derived are suitable aldehyde derivatives of thiophene, furan, pyrrole, imidazole, oxazole, thiazole, pyrazole, pyran, pyridine, pyrimidine, quinoline, isoquinoline, carbazole, and the like. The term "substituted phenoxy" includes phenoxy substituted with from one to three members each selected from the group consisting of lower alkyl, lower alkoxy, nitro, diloweralkylamino, and methylenedioxy (provided that no more than one of said members is methylenedioxy).

The 1,2- and 1,4-addition products of the invention possess cardiovascular activity and are useful as antihypertensive agents as shown by their activity in the spontaneous hypertensive rat test. Preferred dosage ranges are from about 50 to about 100 mg/kg. The 1,2- and 1,4-addition products are also useful as antiarrythmic agents as shown by their activity in diminishing chloroform-induced arrythmia in the mouse. Preferred dosage ranges are from about 100 to about 300 mg/kg. Compounds which have been found to have greatest activity in these tests are 2-phenyl-2-(cycloheptan-3-one)-1,3-dithiane; 2-(2-thienyl)-2-(cyclohexan-3-one)-1,3-dithiane; 2-(2-thienyl)-2-(3-phenylpropiophen-3-one)-1,3-dithiane; and 2-phenyl-2-(2-cyclohepten-1-ol)-1,3-dithiane.

In view of the acitivity of the subject compounds III and IV there is provided herein a method of treating a patient with hypertension or cardiac arrythmia which comprises systemically administering to said patient an effective amount of said compounds, preferably in admixture with a pharmaceutically acceptable carrier.

To prepare the pharmaceutical compositions of this invention, a subject compound of formula III or IV is combined as the active ingredient in intimate admixture with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations such as for example, suspensions, elixirs, and solutions; or carriers such as starches, sugars, diluents, granulating agents, lubricants, binders, disintegrating agents and the like in the case of oral solid preparations such as, for example, powders, capsules, and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions herein will generally contain, per dosage unit, e.g., tablet, capsule, powder, injection, teaspoonful and the like, from about 5 to about 500 mg. of the active ingredient, and preferably, from about 10 to about 250 mg.

The 1,2-addition products of the invention may be converted to the corresponding 1,4-addition products and hence are also useful as intermediates for the production of pharmaceutically-useful compounds. This conversion may be effected by: 1) deprotonating the 1,2-addition product with a deprotonating agent such as a suitable base as previously defined (preferably butyllithium) in an anhydrous aprotic solvent at reduced temperature (about $-75°$ C. to $-100°$ C.) to regenerate the 2-aromatic substituted 1,3-dithiane carbanion; 2) allowing the reaction mixture to warm to ambient temperature and to react; and 3) quenching the reaction with a protonating solvent (preferably water). The 1,4-addition product may be isolated as previously described.

The $\alpha,\beta$-unsaturated ketones of formula I are generally known or may be prepared by known techniques. Cyclic $\alpha,\beta$-unsaturated ketones are also generally known and are described in "Cyclohexadienones" by A. J. Waring in "Advances in Alicyclic Chemistry," Vol. 1, H. Hart and G. J. Karabatsos, Eds., 1969, Archive Press, or may be prepared by techniques described herein. The 2-aromatic substituted 1,3-dithianes of formula II are also generally known or may be prepared by the procedure of D. Seebach, B. W. Erickson, and G. Singh, *J. Org. Chem.*, 31, 4303 (1966).

The subject invention is illustrated by the following examples.

EXAMPLE I

2-Phenyl-2-(cycloheptan-3-one)-1,3-dithiane

A solution of butyllithium (2.4 N, 6.75 ml., 16.2 mmol.) in hexane was added via a syringe to a solution of 2-phenyl-1,3-dithiane (2.88 g., 14.7 mmol.) in anhydrous THF (55 ml.) at $-78°$ C. After stirring for 0.5 hr. at $-78°$ C., 2-cycloheptenone (1.7 g. 15.4 mmol.) in anhydrous THF (10 ml.) was added slowly via a syringe. The mixture was warmed to room temperature and stirred for 1 hour. The reaction was quenched with $H_2O$ (10 ml.), poured into $H_2O$ (500 ml.) and extracted with $Et_2O$. The organic layer was washed with $H_2O$ and saturated aqueous sodium chloride solution, dried over $MgSO_4$, and evaporated in vacuo to give 4.7 g. of a clear yellow gum. This was chromatographed on SilicAR CC-7 (200 g., Mallinckrodt) in hexane. Starting material (2-phenyl-1,3-dithiane) was eluted with 1:4 $CH_2Cl_2$/hexane. Further elution with 1:1 $CH_2Cl_2$/hexane gave 3.60 (76%) of a colorless crystalline mass. Recrystallization from $Et_2O$/hexane afforded the desired product as colorless crystals; m.p. 93°–94° C.

Anal. Calcd. for $C_{17}H_{22}OS_2$: C, 66.62; H, 7.24; Found: C, 66.38; H, 7.06.

EXAMPLE II

2-Phenyl-2-(2-cyclohepten-1-ol)-1,3-dithiane

A solution of butyllithium (2.4 M., 9.0 ml., 21.6 mmol.) in hexane was added via a syringe to a solution of 2-phenyl-1,3-dithiane (3.84 g., 18.6 mmol.) in THF (50 ml.) at −78° C. After stirring for 0.5 hr. at −78° C., 2-cycloheptenone (2.27 g., 20.6 mmol.) in THF (10 ml.) was added slowly via a syringe. Stirring was continued for 0.5 hr., and while at −78° C., H₂O (10 ml.) was added rapidly. The mixture was warmed to room temperature, poured into H₂O, and extracted with diethyl ether. The organic layer was washed with water and satd. NaCl, dried (MgSO₄) and evaporated in vacuo to give 6.1 g. of a clear yellow gum. This was chromatographed on SilicAR CC-7 (200 g., Mallinckrodt) in hexane.

Starting material (2-phenyl-1,3-dithiane) was eluted with 1:4 CH₂Cl₂/hexane. Further elution with 1:1 CH₂Cl₂/hexane gave 4.55 g. (80%) of a colorless crystalline mass. Recrystallization from Et₂O/hexane afforded the desired product as colorless crystals; m.p. 90°–91° C.

Anal. Calcd. for C₁₇H₂₂OS₂: C, 66.62; H, 7.24; Found: C, 66.53; H, 7.15.

EXAMPLE III

Conversion of 2-phenyl-2-(2-cyclohepten-1-ol)-1,3-dithiane to 2-phenyl-2-(cycloheptan-3-one)-1,3-dithiane A solution of butyllithium (2.4 M., 0.3 ml., 0.715 mmol.) in hexane was added via a syringe to a solution of 2-phenyl-2-(2-cyclohepten-1-ol)-1,3-dithiane (0.3 g. 0.650 mmol.) in anhydrous THF (5 ml.) at −78° C. After stirring for 10 min. at −78° C., the mixture was warmed to room temperature and stirred for 2 hours. The reaction was quenched with water (5 ml.), poured into water (15 ml.), and extracted with diethyl ether. The organic layer was washed with H₂O and saturated NaCl solution, dried (MgSO₄), and evaporated in vacuo to give a 200 mg. residue. The residue was chromatographed on SilicAR CC-7 (12 g.) in hexane. Starting material (2-phenyl-1,3-dithiane) was eluted with 1:4 CH₂Cl₂/hexane. Further elution with 1:1 CH₂Cl₂/hexane gave 2-phenyl-2-(cycloheptan-3-one)-1,3-dithiane as a crystalline mass. Recrystallization from diethyl ether/hexane yielded the desired product; m.p. 93°–94° C.

EXAMPLE IV

Following the procedure of Example I, but substituting for the 2-phenyl-1,3-dithiane and cycloheptanone used therein, equivalent amounts of the suitable materials, there are produced the following 1,4-addition products:

2-(2-thienyl)-2-(cyclohexan-3-one)-1,3-dithiane, m.p. 125°–126° C.;
2-phenyl-2-(cyclopentan-3-one)-1,3-diathane, m.p. 128°–130° C.;
2-phenyl-2-(cyclohexan-3-one)-1,3-dithiane, m.p. 124.5°–125.5° C.;
2-phenyl-2-(1-methylcyclohexan-3-one)-1,3-dithiane, m.p. 108.5°–110° C.;
2-phenyl-2-(2-methylcyclohexan-3-one)-1,3-dithiane, m.p. 111.5°–113° C.;
2-phenyl-2-(1-methylcyclopentan-3-one)-1,3-dithiane, m.p. 75°–75.5° C.;
2-naphthyl-2-(cyclohexan-3-one)-1,3-dithiane, m.p. 105°–107° C.; and
2-(2-thienyl)-2-(3-phenylpropiophen-3-one)-1,3-dithiane; m.p. 134°–135° C.

EXAMPLE V

Following the procedure of Example I, but substituting for the 2-phenyl-1,3-dithiane and cycloheptanone used therein, equivalent amounts of the suitable materials, there are produced the following 1,4-addition products:

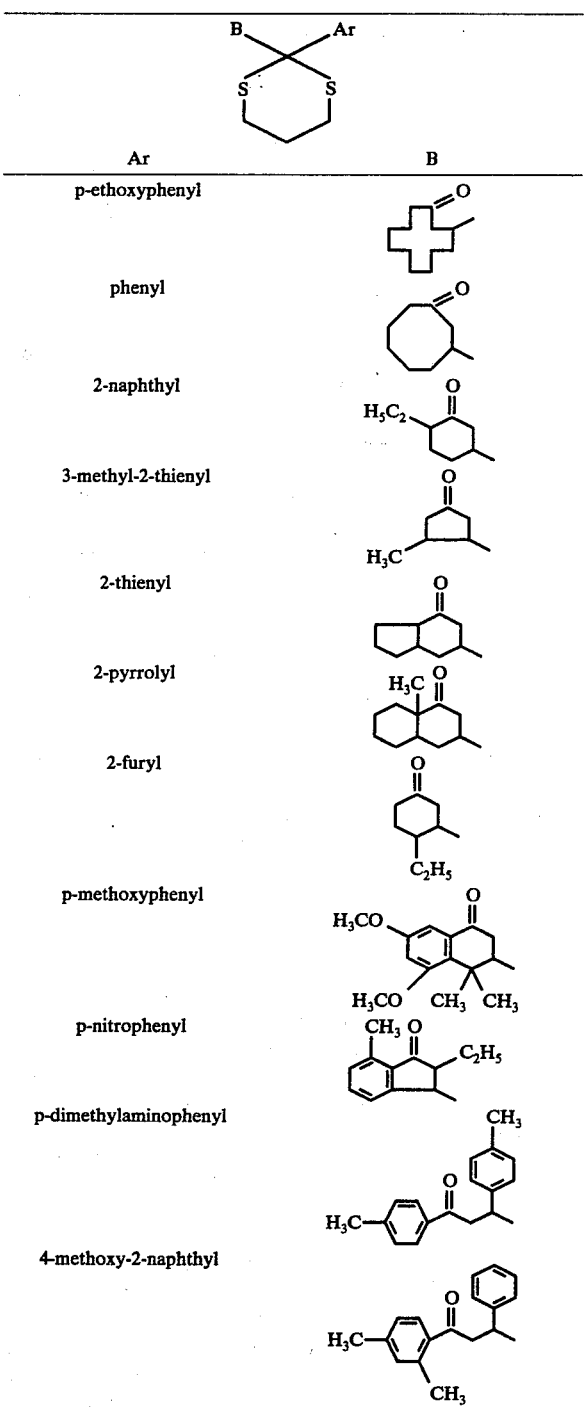

-continued

| Ar | B |
|---|---|
| 2-imidazolyl | cyclohexanone-2-CH₂– |
| 2-oxazolyl | cyclopentanone-2-CH₂– |
| 2-thiazolyl | cycloheptanone-2-CH₂– |
| 4-pyrazolyl | decalone-CH₂– |
| 2-pyridyl | hydrindanone-CH₂– |
| 2-quinolyl | (ethoxy, methyl-substituted octahydronaphthalenone-CH₂–) |
| 3,4-methylenedioxyphenyl | (phenoxy-substituted octahydronaphthalenone-CH₂–) |
| 2-(benzothienyl) | 3-methylcyclohexanone |
| 2-(4,5,6,7-tetrahydrobenzothienyl) | 3-methylcyclopentanone |
| 4,5-methylenedioxy-2-naphthyl | 3-methylcyclohexanone |
| 8-nitro-2-naphthyl | 3-methylcyclopentanone |

EXAMPLE VI

Following the procedure of Example II, but substituting for the 2-phenyl-1,3-dithiane and cycloheptanone used therein, equivalent amounts of the suitable materials, there are produced the following 1,2-addition products:

| Ar | B |
|---|---|
| p-ethoxyphenyl | 1-hydroxycyclohexyl (bicyclic) |
| phenyl | 1-hydroxycycloheptenyl |
| 2-naphthyl | 1-hydroxy-4-ethylcyclohexenyl |
| 3-methyl-2-thienyl | 1-hydroxy-methylcyclopentenyl |
| 2-thienyl | 1-hydroxyindanyl |
| 2-pyrrolyl | 1-hydroxy-methyl-decalinyl |
| 2-furyl | 1-hydroxy-ethylcyclohexenyl |
| p-methoxyphenyl | dimethoxy-dimethyl-hydroxytetralinyl |
| p-nitrophenyl | 1-hydroxy-ethyl-methylindanyl |
| p-dimethylaminophenyl | bis(p-tolyl)hydroxypropenyl |
| 4-methoxy-2-naphthyl | dimethylphenyl-hydroxymethyl-propenyl |
| 2-imidazolyl | 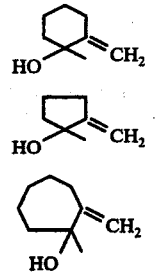 |
| 2-oxazolyl | 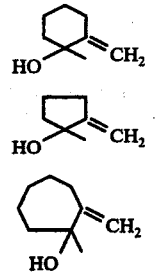 |
| 2-thiazolyl | 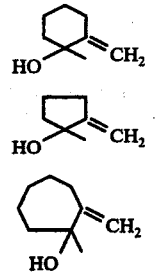 |
| 4-pyrazolyl | 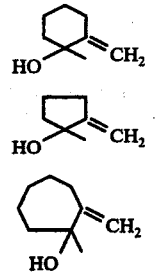 |
| 2-pyridyl | 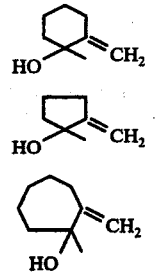 |

-continued

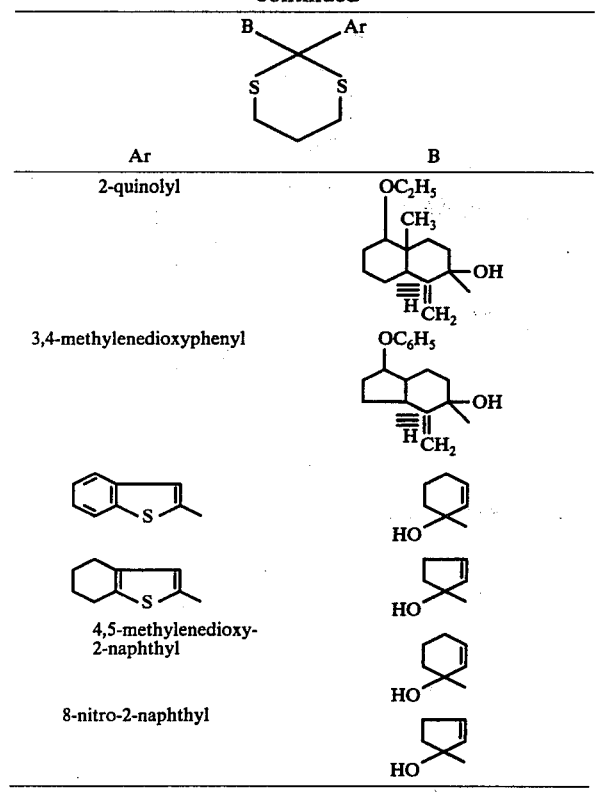

| Ar | B |
| --- | --- |
| 2-quinolyl | 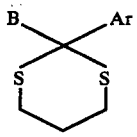 |
| 3,4-methylenedioxyphenyl | 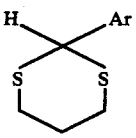 |
| 4,5-methylenedioxy-2-naphthyl | |
| 8-nitro-2-naphthyl | |

EXAMPLE VII

Following the procedure of Example III, but substituting for the 2-phenyl-2-(2-cyclohepten-1-ol)-1,3-dithiane used therein an equivalent amount of a 1,2-addition product of Example VI, there are produced the 1,4-addition products of Example V.

The above examples have been given by way of illustration only and not to limit the scope of the present invention, which scope is defined in the appended claims.

What is claimed is:

1. A method of preparing a compound of the formula:

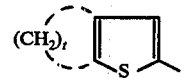

which comprises deprotonating a 2-aromatic substituted 1,3-dithiane of the formula:

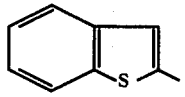

at a temperature between $-75°$ C and $-100°$ C, in the presence of a base in an aprotic anhydrous solvent, reacting the 2-carbanion formed with an $\alpha,\beta$-unsaturated ketone selected from the group consisting of:

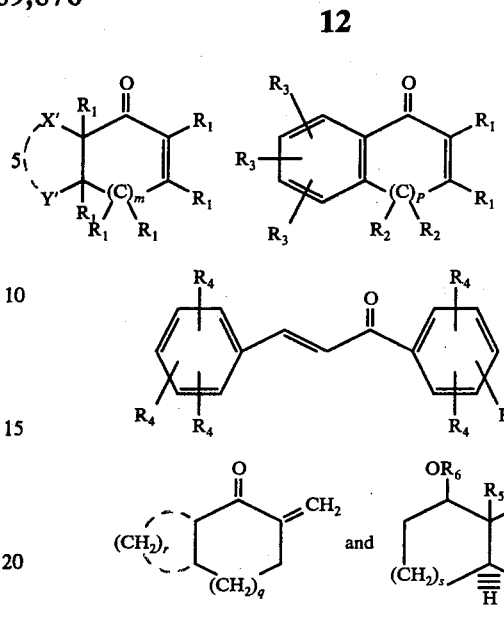

and then either a. adding a protonating solvent to produce the 1,2-addition product; or b. allowing the mixture to warm to ambient temerature, followed by addition of a protonating solvent to produce the 1,4-addition product; wherein Ar is a member selected from the group consisting of phenyl, phenyl substituted with from one to three members each selected from the group consisting of lower alkyl, lower alkoxy, nitro, diloweralkylamino, and methylenedioxy, provided that not more than one of said members is methylenedioxy, phenoxy, and substituted phenoxy, wherein the substituent is one to three members selected from the group consisting of lower alkyl, lower alkoxy, nitro, diloweralkylamino and methylenedioxy; naphthyl; naphthyl substituted with from one to three members each selected from the group consisting of lower alkyl, lower alkoxy, nitro, diloweralkylamino, methylenedioxy, phenoxy and substituted phenoxy, wherein the substituent is one to three members selected from the group consisting of lower alkyl, lower alkoxy, nitro, diloweralkylamino and methylenedioxy, provided that no more than one of said members is methylenedioxy; 2-thienyl; 2-thienyl substituted with from one to three lower alkyls;

wherein $t$ is an integer from 3 to 5; and and
each $R_1$ is a member selected from the group consisting of hydrogen and lower alkyl; $X'$ and $Y'$ taken separately are each a member selected from the group consisting of hydrogen and lower alkyl; $X'$ and $Y'$ taken together is $-(CH_2)n-$, where $n$ is an integer from 2 to 6; $m$ is an integer from 0 to 7; each $R_2$ is lower alkyl;

$p$ is an integer from 0 to 3; each $R_3$ is a member selected from the group consisting of hydrogen, lower alkyl, lower alkoxy, nitro, diloweralkylamino, and methylenedioxy, provided that not more than one $R_3$ is methylenedioxy, phenoxy, and substituted phenoxy with from one to three members each selected from the group consisting of lower alkyl, lower alkoxy, nitro, diloweralkylamino, and methylenedioxy;

each $R_4$ is a member selected from the group consisting of hydrogen, lower alkyl, lower alkoxy, nitro, diloweralkylamino, and methylenedioxy, provided that not more than one $R_4$ on each phenyl ring is methylenedioxy, phenoxy, and substituted phenoxy with from one to three members each selected from the group consisting of lower alkyl, lower alkoxy, nitro, diloweralkylamino and methylenedioxy;

$q$ is an integer from 0 to 2 and $r$ is an integer from 3 to 6; and

B is a member selected from the group consisting of:

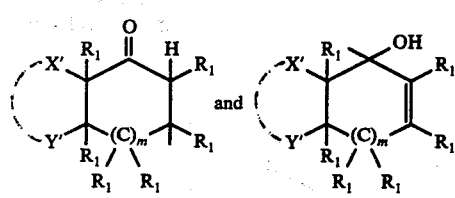

in the 1,4-addition product    in the 1,2-addition product

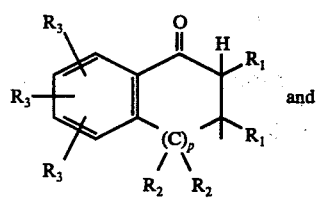

in the 1,4-addition product

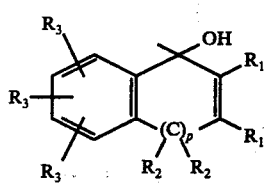

in the 1,2-addition product

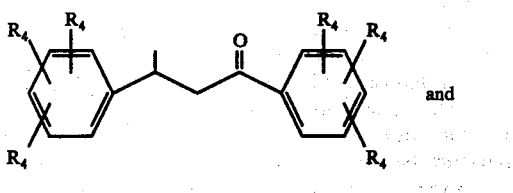

in the 1,4-addition product

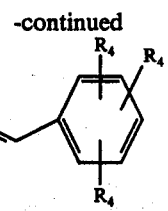

in the 1,2-addition product

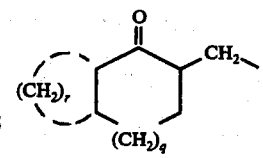

in the 1,4-addition product

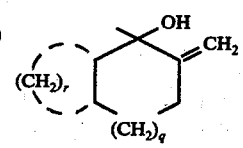

in the 1,2-addition product

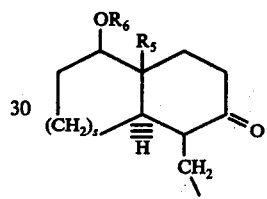

in the 1,4-addition product

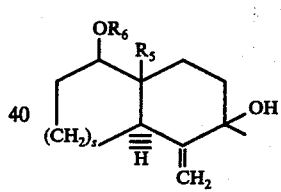

in the 1,2-addition product and $R_5$ is a member selected from the group consisting of hydrogen and lower alkyl; and $R_6$ is a member selected from the group consisting of lower alkyl and aryl.

2. The method of claim 1, which produces solely the 1,4-addition product.

3. The method of claim 1, which produces solely the 1,2-addition product.

4. The method of claim 1, wherein deprotonating the 2-aromatic substituted 1,3-dithiane is accomplished by reacting said 2-aromatic substituted 1,3-dithiane with a base selected from the group consisting of butyllithium, alkali metal hydrides, and lithium diisopropylamide in an anhydrous aprotic solvent selected from the group consisting of tetrahydrofuran and 1,2-dimethoxyethane, wherein said reduced temperature is from about −75° C. to about −100° C., wherein said ambient temperature is above about 10° C., and wherein said protonating solvent is water.

5. The method of claim 4, wherein the 2-aromatic substituted 1,3-dithiane is a compound of formula:

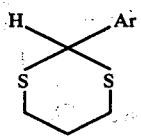

wherein Ar is a member selected from the group consisting of phenyl, phenyl substituted with from one to three members each selected from the group consisting of lower alkyl, lower alkoxy, nitro, diloweralkylamino and methylenedioxy, provided that not more than one of said members is methylenedioxy, phenoxy and substituted phenoxy, wherein the substituent is one to three members selected from the group consisting of lower alkyl, lower alkoxy, nitro, diloweralkylamino and methylenedioxy; naphthyl; naphthyl substituted with from one to three members each selected from the group consisting of lower alkyl, lower alkoxy, nitro, diloweralkylamino, methylenedioxy, phenoxy, and substituted phenoxy, wherein the substituent is one to three members selected from the group consisting of lower alkyl, lower alkoxy, nitro, diloweralkylamino and methylenedioxy, provided that no more than one of said members is methylenedioxy; 2-thienyl, 2-thienyl substituted with from one to three lower alkyls;

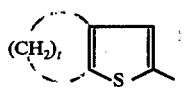

wherein $t$ is an integer from 3 to 5; and;

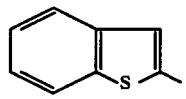

and
wherein the $\alpha,\beta$-unsaturated ketone is a member selected from the group consisting of:
a. a compound of formula:

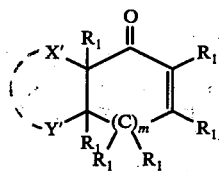

wherein: each $R_1$ is a member selected from the group consisting of hydrogen and lower alkyl; X' and Y' taken separately are each a member selected from the group consisting of hydrogen and lower alkyl; X' and Y' taken together is $-(CH_2)_n-$, where n is an integer from 2 to 6; and m is an integer from 0 to 7;
b. a compound of formula:

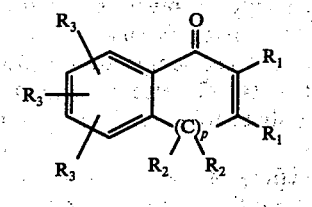

wherein: each $R_1$ is a member selected from the group consisting of hydrogen and lower alkyl; each $R_2$ is lower alkyl;
$p$ is an integer from 0 to 3; and
each $R_3$ is a member selected from the group consisting of hydrogen, lower alkyl, lower alkoxy, nitro diloweralkylamino, and methylenedioxy, provided that no more than one $R_3$ is methylenedioxy, phenoxy, and substituted phenoxy,
wherein the substituent is one to three members selected from the group consisting of lower alkyl, lower alkoxy, nitro, diloweralkylamino and methylenedioxy;
c. a compound of formula:

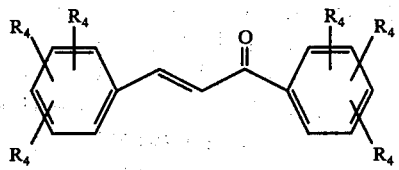

wherein each $R_4$ is a member selected from the group consisting of hydrogen, lower alkyl, lower alkoxy, nitro, diloweralkylamino, and methylenedioxy, provided that not more than one $R_4$ on each phenyl ring is methylenedioxy, phenoxy, and substituted phenoxy,
wherein the substituent is one to three members selected from the group consisting of lower alkyl, lower alkoxy, nitro, diloweralkylamino and methylenedioxy;
d. a compound of formula:

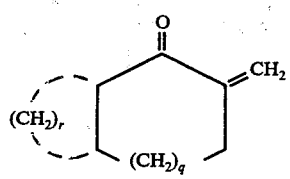

wherein $q$ is an integer from 0 to 2 and $r$ is an integer from 3 to 6; and
e. a compound of formula:

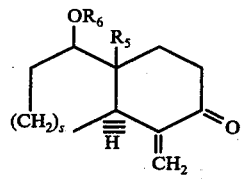

wherein $s$ is an integer from 0 to 2;
$R_5$ is a member selected from the group consisting of hydrogen and lower alkyl; and $R_6$ is a member selected from the group consisting of lower alkyl and aryl.

6. A method for converting the 1,2-addition product of claim 1 of a 2-aromatic substituted 1,3-dithiane and an $\alpha,\beta$-unsaturated ketone into the corresponding 1,4-addition product which comprises the steps of:
a. deprotonating said 1,2-addition product at a temperature between $-75°$ and $-100°$ C in an anhydrous aprotic solvent to regenerate the 2-carbanion of the 2-aromatic substituted 1,3-dithiane and form a reaction mixture;

b. allowing the reaction mixture to warm to ambient temperature and to react at ambient temperature; and c. adding a protonating solvent to said reaction mixture at ambient temperature to produce the 1,4-addition product.

7. The method of claim 6, wherein deprotonating the 1,2-addition product is accomplished by reacting said 1,2-addition product with a base selected from the group consisting of butyllithium, alkali metal hydrides, and lithium diisopropylamide in an anhydrous aprotic solvent selected from the group consisting of tetrahydrofuran and 1,2-dimethoxyethane, wherein said reduced temperature is from about −75° C. to about −100° C., wherein said ambient temperature is above about 10° C., and wherein said protonating solvent is water.

8. The method of claim 7, wherein the 2-aromatic substituted 1,3-dithiane is a compound of formula:

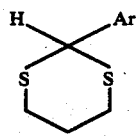

wherein Ar is a member selected from the group consisting of phenyl, phenyl substituted with from one to three members each selected from the group consisting of lower alkyl, lower alkoxy, nitro, diloweralkylamino, and methylenedioxy, provided that not more than one of said members is methylenedioxy, phenoxy, and substituted phenoxy,
  wherein the substituent is one to three members selected from the group consisting of lower alkyl, lower alkoxy, nitro, diloweralkylamino and methylenedioxy; naphthyl; naphthyl substituted with from one to three members selected from the group consisting of lower alkyl, lower alkoxy, nitro, diloweralkylamino, methylenedioxy, phenoxy, and substituted phenoxy,
  wherein the substituent is one to three members selected from the group consisting of lower alkyl, lower alkoxy, nitro, diloweralkyamino and methylenedioxy, provided that no more than one of said members is methylenedioxy; 2-thienyl; 2-thienyl substituted with from one to three lower alkyls;

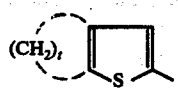

wherein $t$ is an integer from 3 to 5; and

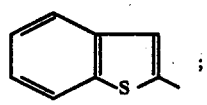

and
wherein the α,β-unsaturated ketone is a member selected from the group consisting of:
a. a compound of formula:

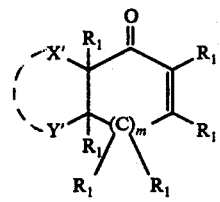

wherein: each $R_1$ is a member selected from the group consisting of hydrogen and lower alkyl; X' and Y' taken separately are each a member selected from the group consisting of hydrogen and lower alkyl; X' and Y' taken together is —$(CH_2)_n$—, where $n$ is an integer from 2 to 6; and $m$ is an integer from 0 to 7;

b. a compound of formula:

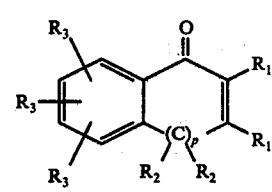

wherein: each $R_1$ is a member selected from the group consisting of hydrogen and lower alkyl; each $R_2$ is lower alkyl;
$p$ is an integer from 0 to 3; and each $R_3$ is a member selected from the group consisting of hydrogen, lower alkyl, lower alkoxy, nitro, diloweralkylamino, and methylenedioxy, provided that not more than one $R_3$ is methylenedioxy, phenoxy and substituted phenoxy,
wherein the substituent is one to three members selected from the group consisting of lower alkyl, lower alkoxy, nitro, diloweralkylamino and methylenedioxy;

c. a compound of formula:

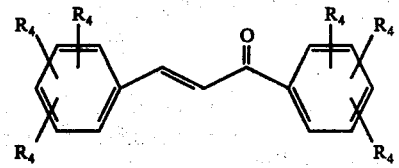

wherein, each $R_4$ is a member selected from the group consisting of hydrogen, lower alkyl, lower alkoxy, nitro, diloweralkylamino, and methylenedioxy, provided that not more than one $R_4$ on each phenyl ring is methylenedioxy, phenoxy, and substituted phenoxy,
wherein the substituent is one to three members selected from the group cnsisting of lower alkyl, lower alkoxy, nitro, diloweralkylamino and methylenedioxy;

d. a compound of formula:

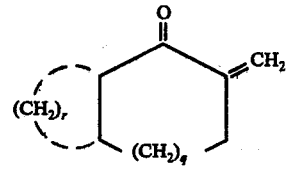

wherein $q$ is an integer from 0 to 2 and $r$ is an integer from 3 to 6; and e. a compound of formula

[Structure with $OR_6$, $R_5$, $(CH_2)_s$, H, CH$_2$, =O]

wherein $s$ is an integer from 0 to 2;
$R_5$ is a member selected from the group consisting of hydrogen and lower alkyl; and R is a member selected from the group consisting of lower alkyl and aryl.

9. A compound of formula:

[Structure showing B and Ar attached to carbon with two S atoms in a ring]

wherein, Ar is a member selected from the group consisting of phenyl, phenyl substituted with from one to three members each selected from the group consisting of lower alkyl, lower alkoxy, nitro, diloweralkylamino, and methylenedioxy, provided that not more than one of said members is methylenedioxy, phenoxy, and substituted phenoxy, wherein the substituent is one to three members selected from the group consisting of lower alkyl, lower alkoxy, nitro, diloweralkylamino and methylenedioxy; naphthyl; naphthyl substituted with from one to three members each selected from the group consisting of lower alkyl, lower alkoxy, nitro, diloweralkylamino, methylenedioxy, phenoxy, and substituted phenoxy, wherein the substituent is one to three members selected from the group consisting of lower alkyl, lower alkoxy, nitro, diloweralkylamino and methylenedioxy, provided that no more than one of said members is methylenedioxy; 2-thienyl; 2-thienyl substituted with from one to three lower alkyls;

[Structure with $(CH_2)_t$ and S in ring]

wherein $t$ is an integer from 3 to 5; and

[Benzothiophene structure]

and
wherein B is a member selected from the group consisting of:

a) [Structure with $R_1$, X', Y', $(C)_m$, O]

wherein; each $R_1$ is a member selected from the group consisting of hydrogen and lower alkyl; X' and Y' taken separately are each a member selected from the group consisting of hydrogen and loweralkyl; X' and Y' taken together is —(CH$_2$)$_n$—, where $n$ is an integer from 2 to 6; and $m$ is an integer from 0 to 7;

b) [Structure with $R_3$, $R_1$, $(C)_p$, $R_2$, O]

wherein; each $R_1$ is a member selected from the group consisting of hydrogen and lower alkyl; each $R_2$ is lower alkyl;
$p$ is an integer from 0 to 3; and each $R_3$ is a member selected from the group consisting of hydrogen, lower alkyl, lower alkoxy, nitro, diloweralkylamino, and methylenedioxy; provided that not more than one $R_3$ is methylenedioxy, phenoxy, and substituted phenoxy, wherein the substituent is one to three members selected from the group consisting of lower alkyl, lower alkoxy, nitro, diloweralkylamino and methylenedioxy;

c) [Structure with two phenyl rings substituted with $R_4$, connected via CH-CH$_2$-C(=O)]

wherein each $R_4$ is a member selected from the group consisting of hydrogen, lower alkyl, lower alkoxy, nitro, diloweralkylamino, and methylenedioxy, provided that not more than one $R_4$ on each phenyl ring is methylenedioxy, phenoxy and substituted phenoxy, wherein the substituent is one to three members selected from the group consisting of lower alkyl, lower alkoxy, nitro, diloweralkylamino and methylenedioxy;

d) [Structure with $(CH_2)_r$, $(CH_2)_q$, CH$_2$, O]

wherein, $q$ is an integer from 0 to 2 and $r$ is an integer from 3 to 6; and

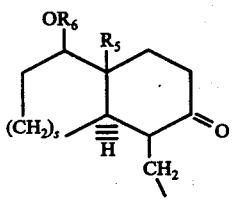

e)

wherein s in an integer from 0 to 2;

$R_5$ is a member selected from the group consisting of hydrogen and lower alkyl; and $R_6$ is a member selected from the group consisting of lower alkyl and aryl.

10. The compound of claim 9, which is 2-phenyl-2-(cycloheptan-3-one)-1,3-dithiane.

11. The compound of claim 9, which is 2-(2-thienyl)-2-(cyclohexan-3-one)-1,3-dithiane.

12. The compound of claim 9, which is 2-(2-thienyl)-2-(3-phenylpropiophen-3-one)-1,3-dithiane.

13. A compound of formula:

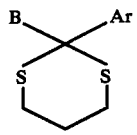

wherein Ar is a member selected from the group consisting of phenyl, phenyl substituted with from one to three members each selected from the group consisting of lower alkyl, lower alkoxy, nitro, diloweralkylamino, and methylenedioxy, provided that nor more than one of said members is methylenedioxy, phenoxy, and substituted phenoxy, wherein the substituent is one to three members selected from the group consisting of lower alkyl, lower alkoxy, nitro, diloweralkylamino and methylenedioxy; napthyl; naphthyl substituted with from one to three members each selected from the group consisting of lower alkyl, lower alkoxy, nitro, diloweralkylamino, methylenedioxy, phenoxy, and substituted phenoxy, wherein the substituent is one to three members selected from the group consisting of lower alkyl, lower alkoxy, nitro diloweralkylamino and methylenedioxy, provided that no more than one of said members is methylenedioxy; 2-thienyl; 2-thienyl substituted with from one to three lower alkyls;

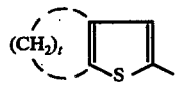

wherein, t is an integer from 3 to 5; and

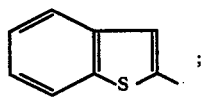

and wherein, B is a member selected from the group consisting of:

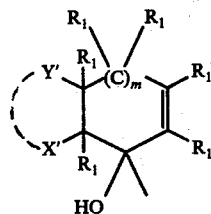

wherein: each $R_1$ is a member selected from the group consisting of hydrogen and lower alkyl; X' and Y' taken separately are each a member selected from the group consisting of hydrogen and lower alkyl; X' and Y' taken together is —$(CH_2)_n$—, where n is an integer from 2 to 6; and m is an integer from 0 to 7;

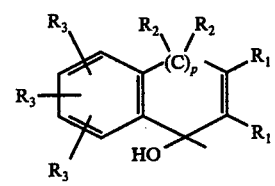

b)

wherein, each $R_1$ is a member selected from the group consisting of hydrogen and lower alkyl; $R_2$ is lower alkyl;

p is an integer from 0 to 3; and each $R_3$ is a member selected from the group consisting of hydrogen, lower alkyl, lower alkoxy, nitro, diloweralkylamino, and methylenedioxy, provided that not more than one $R_3$ is methylenedioxy, phenoxy, and substituted phenoxy, wherein the substituent is one to three members selected from the group consisting of lower alkyl, lower alkoxy, nitro, diloweralkylamino and methylenedioxy;

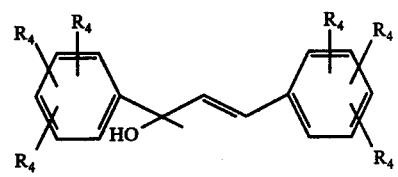

c)

wherein each $R_4$ is a member selected from the group consisting of hydrogen, lower alkyl, lower alkoxy, nitro, diloweralkylamino, and methylenedioxy, provided that not more than one $R_4$ on each phenyl ring is methylenedioxy, phenoxy, and substituted phenoxy, wherein the substituent is one to three members selected from the group consisting of lower alkyl, lower alkoxy, nitro, diloweralkylamino and methylenedioxy;

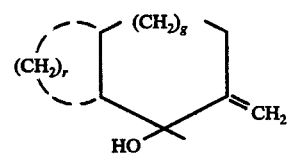

d)

wherein q is an integer from 0 to 2 and r is an integer from 3 to 6; and

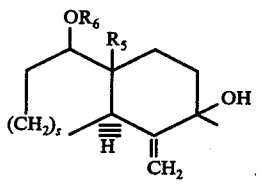

e)

wherein s is an integer from 0 to 2;
$R_5$ is a member selected from the group consisting of hydrogen and lower alkyl; an
$R_6$ is a member selected from the group consisting of lower alkyl and aryl.

14. The compound of claim 13, which is 2-phenyl-2-(2-cyclohepten-1-ol)-1,3-dithiane.

* * * * *

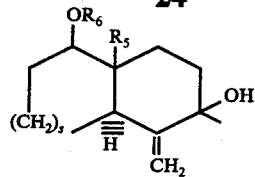

e)

wherein s is an integer from 0 to 2;
$R_5$ is a member selected from the group consisting of hydrogen and lower alkyl; an
$R_6$ is a member selected from the group consisting of lower alkyl and aryl.

14. The compound of claim 13, which is 2-phenyl-2-(2-cyclohepten-1-ol)-1,3-dithiane.

* * * * *

UNITED STATES PATENT AND TRADEMARK OFFICE
CERTIFICATE OF CORRECTION

PATENT NO. : 4,089,876
DATED : May 16, 1978
INVENTOR(S) : Vinayak V. Kane

It is certified that error appears in the above-identified patent and that said Letters Patent are hereby corrected as shown below:

At Column 6, Line 38, "herein" should be -- therein --.
At Column 19, Line 16, "and R is" should be -- and $R_6$ is --.
At Column 21, Line 36, "nor" should be -- not --.
At Column 23, Line 11, "an" should be -- and --.
Delete Column 24 in its entirety.

Signed and Sealed this

Seventh Day of November 1978

[SEAL]

Attest:

RUTH C. MASON
Attesting Officer

DONALD W. BANNER
Commissioner of Patents and Trademarks